United States Patent
Gavronsky

(10) Patent No.: US 6,231,584 B1
(45) Date of Patent: May 15, 2001

(54) ACUPUNCTURE DEVICE WITH IMPROVED NEEDLE GUIDE TUBE

(76) Inventor: Stas Gavronsky, 39 Wayland Hills Rd., Wayland, MA (US) 01778

( * ) Notice: Subject to any disclaimer, the term of this patent is extended or adjusted under 35 U.S.C. 154(b) by 0 days.

(21) Appl. No.: 09/590,032

(22) Filed: Jun. 7, 2000

(51) Int. Cl.[7] ................................................. A61B 17/34
(52) U.S. Cl. ........................................ 606/189; 128/907
(58) Field of Search .................................. 606/189, 185, 606/187, 188; 600/566–567; 128/907

(56) References Cited

U.S. PATENT DOCUMENTS

| | | | |
|---|---|---|---|
| 3,943,932 | * | 3/1976 | Woo ....................................... 606/189 |
| 4,479,291 | * | 10/1984 | Yamada ................................. 606/187 |
| 4,479,496 | * | 10/1984 | Hsu ........................................ 606/189 |
| 4,580,566 | * | 4/1986 | Hsu ........................................ 606/189 |
| 4,950,279 | * | 8/1990 | Chang .................................... 606/189 |
| 5,624,460 | * | 4/1997 | Yoo ........................................ 606/189 |
| 6,106,539 | * | 8/2000 | Fortier ................................... 606/185 |

* cited by examiner

Primary Examiner—Kennedy Schaetzle
Assistant Examiner—Kristen Droesch

(57) ABSTRACT

An acupuncture device consists of an acupuncture needle and a guide tube having a longitudinal slot or notch at the upper end of the tube, which is wider than the diameter of the needle handle. A practitioner can easily secure the upper portion of the handle in this notch by pressing on the handle of the needle with an index finger. In the case of angular insertions, the practitioner can maintain a desirable diagonal position of the needle inside the guide tube. The acupuncture operation is facilitated by making a larger portion of the needle handle projecting from the guide tube through the notch. According to another embodiment, the device is provided with a sleeve of a C-shaped configuration, which is fit onto the upper end of the guide tube. When the open part of the C-shaped configuration does not coincide with the aforementioned notch, and the handle of the needle stays inside the guiding tube, the whole device can be used in a conventional fashion. When the open part of the C-shaped configuration coincides with the aforementioned notch, the needle handle can be pushed through the notch, and when the sleeve is turned so that the groove is overlapped, the needle handle will be deflected and fixed between the lower edge of the sleeve and the bottom of the notch.

7 Claims, 2 Drawing Sheets

ACUPUNCTURE DEVICE WITH IMPROVED NEEDLE GUIDE TUBE

FIELD OF THE INVENTION

The present invention relates to the field of needle therapy, in particular to an acupuncture device with an improved needle guide tube.

BACKGROUND OF THE INVENTION

Acupuncture guide tubes are widely used in the practice of acupuncture to minimize discomfort during needle insertion. The guide tube allows quick insertion of an acupuncture needle through the epidermis. An example of a guide tube is the one shown in U.S. Pat. No. 5,792,171 issued in 1998 to Burdenko, et al. Fast puncturing of the patient's skin is important for pain-free insertion. There is typically 3–5 mm clearance between the upper end of the guide tube and the top of the handle of an acupuncture needle, which protrudes above the tube. The practitioner taps on the handle of the needle downward with his/her index finger while supporting the tube with the other hand. The needle, which has been resting on the surface of the patient's skin prior to insertion, is now inserted 3–5 mm through the skin into the acupuncture point. The guide tube has a diameter, which is bigger than the diameter of the handle of the acupuncture needle. This allows the removal of the guide tube after the insertion. On one hand, the relatively big diameter of the tube, in comparison with the shaft of the needle, provides more comfort for the patient by creating mild pressure around the acupuncture point and by providing firmness to the skin around that point. This feature is important for fast, pain-free insertion. On the other hand, the relatively big diameter of the tube compromises the precision of the insertion. This is because the tip of the needle is rarely in the center of the bottom opening of the tube prior to insertion, but at the sides, leaning against the inside tubular wall. The needle then tends to take diagonal orientation in respect to the tubular longitudinal axis. The tip of the needle, which rests on the skin, is at the bottom tubular wall opposite to the handle.

The practitioner is often unaware about an exact position of the needle. Hence, the angle at which the needle is inserted into the point is unpredictable. Furthermore, when the practitioner attempts to insert a needle at sharp angles, such as on the face or head of the patient, the acupuncture needle tends to slide downward, out of the guide tube. This condition is shown in FIG. 1, which illustrates the positions of a needle guide tube 10 and an acupuncture needle 13. As can be seen from FIG. 1, when the needle 13 is inserted at a sharp angle to the surface of the skin S, a very little clearance C is left between the upper portion of the tube and the handle H of the needle 13. This makes the regular insertion technique very uncomfortable, if not impossible. Also, the clearance C is too small for full penetration of the tip of the needle through the epidermis. As a result, the patient may feel more pain than is necessary.

There are two reasons that contribute to the reduction of this clearance C on top. One reason has to do with the thickness T of the tubular wall. The acupuncture needle 13 has to go a little forward and downward, over the small threshold formed by the bottom edge E of the guide tube 10, to touch the skin S. The other reason has to do with the fact that in the inclined position (angular insertion) shown in FIG. 1, both the tip F of the needle 13 and the handle H of the needle are now against the same tubular wall. This contributes to the additional "slip out" of the needle at the skin S. It would be better, if the handle of the needle stayed at the opposite wall (diagonally), thus shortening the distance that the needle has to travel to reach the skin. But it is often hard to maintain this position of the handle during angular insertions because of the pressing of the handle H of the needle 13 against upper wall with index finger: there is not enough space between the handle H and the skin S. Sometimes, acupuncture insertions have to be performed against gravity. Needling of the points at the cervical spine with the patient in a sitting position is just one example of this. The acupuncture needle tends to slide out of the guide tube during such insertions, and regular insertion technique becomes impossible.

OBJECTS OF THE INVENTION

It is an object of the present invention to provide an acupuncture device with an improved needle guide tube which allows convenient insertion of the needle irrespective of the angle of the needle in respect to the surface of the patient's skin, ensures clearance between the upper end of the needle handle and the upper end of the guide tube sufficient for full and painless penetration of the needle into the patient's skin in angular insertions, and has the means for maintaining the needle in a correct position with respect to the inner walls of the guide tube. Another object is to provide means for convenient and reliable insertion of a needle irrespective of the patient's position.

SUMMARY OF THE INVENTION

The acupuncture device of the present invention consists of an acupuncture needle and a guide tube having a longitudinal slot or notch at the upper end of the tube which is wider than the diameter of the needle handle. A practitioner can easily secure the upper portion of the handle in this notch by pressing on the handle of the needle with his/her index finger. In angular insertions, the practitioner can maintain the desirable diagonal position of the needle inside the guide tube. The acupuncture procedure is facilitated due to the fact that a larger portion of the needle handle projects from the guide tube through the notch. According to another embodiment, the device is provided with a sleeve of a C-shaped configuration, which is fit onto the upper end of the guide tube. When the open part of the C-shaped configuration does not coincide with the aforementioned notch and the handle of the needle stays inside the guide tube, the whole device can be used in a usual fashion. When the open part of the C-shaped configuration coincides with the aforementioned notch, the needle handle can be pushed through the notch and when the sleeve is turned so that the groove is overlapped, the needle handle is deflected and fixed between the lower edge of the sleeve and the bottom of the notch.

Detailed Description of the Invention

Figure 1:
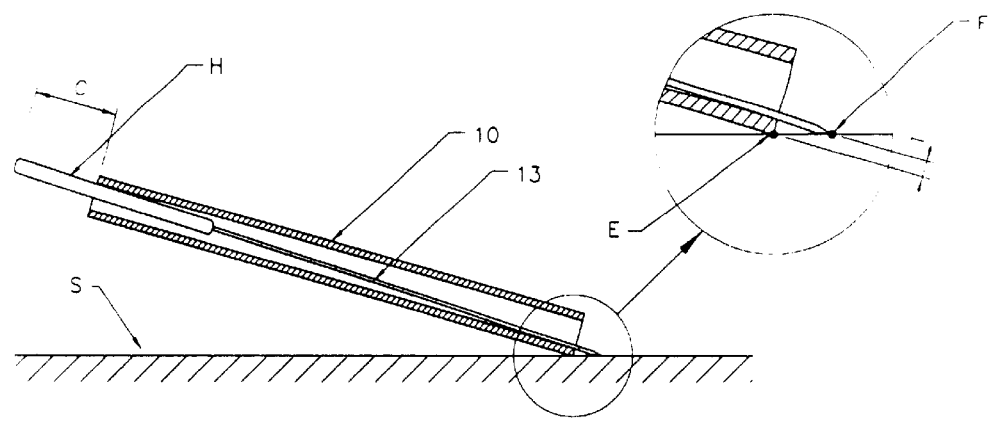
FIG. 1 is a sectional view of an acupuncture device with a conventional guide tube.
Figure 2:
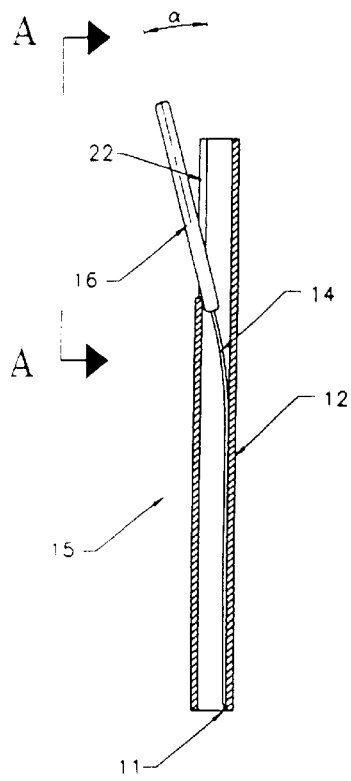
FIG. 2 is a side sectional view of the acupuncture device of the present invention with the acupuncture needle at a substantially vertical position with respect to the patient's skin.
Figure 4:
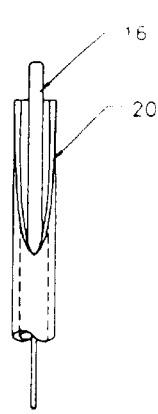
FIG. 4 is a view of the device of FIG. 2 in the direction of arrow A with a triangular notch in the guide tube.

An acupuncture device of the invention is shown in FIGS. 2 and 4, where FIG. 2 is a side sectional view of the device and FIG. 4 is a view of the device of FIG. 2 in the direction of arrow A. The device as a whole is designated by reference numeral 15. It consists of a guide tube 12 and an acupuncture needle 14 with a needle handle 16. Since the needle 14 with the handle 16 is longer than the guide tube 12, the upper end of the handle 16 projects from the upper end of the guide tube.

Figure 3:
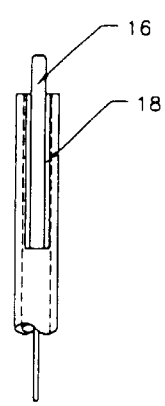
FIG. 3 is a fragmental view similar to FIG. 4 with a rectangular notch.

The upper end of the guide tube 12 has a slot or notch (FIG. 4) which may be a triangular shape notch 20 shown in FIG. 4, or a rectangular shape notch 18 shown in FIG. 3. When there is a rectangular notch 18, the width of the notch 18 should slightly exceed the diameter of the needle handle 16 in order to ensure free movement of the needle handle 16 inside the notch 18. The slot or notch may have a depth of 12 mm or more.

As can be seen from FIG. 2 or FIG. 4, the upper edge of the guide tube 12 can be chamfered or beveled at an angle a in the area of the aforementioned notch 18 or 20. The beveled edge 22 (FIG. 2) will facilitate manipulation of the needle handle 16.

Figure 5:
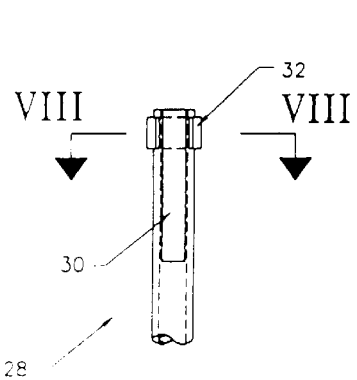
FIG. 5 is a side view of a device of the invention with a sleeve for controlling the position of the needle with respect to the guide tube walls; the needle is not shown.
Figure 6:
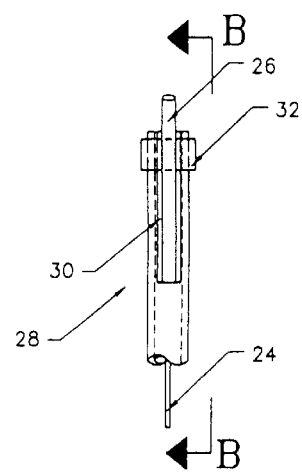
FIG. 6 is a view of the device of FIG. 5 with the sleeve overlapping the slot of the guide tube for fixing the needle in a diagonal position inside the guide tube.
Figure 7:
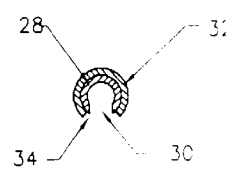
FIG. 7 is cross-sectional view along line VIII—VIII of FIG. 5.

FIGS. 5 and 6 illustrate another embodiment of the acupuncture device of the invention which consists of an acupuncture needle 24 with a handle 26, a guide tube 28 with a slot or notch 30 of the same type as in the embodiment of FIGS. 2 through 4, and a handle position control sleeve 32 slidingly fit onto the upper end of the guide tube 28. The sleeve 32 can be cut from the same piece of material as the guide tube 28 and has a C-shaped cross section formed by cutting a through longitudinal slit 34 in the wall of the sleeve. This is shown in FIG. 7 which is a cross-sectional view along line VIII—VIII of FIG. 5. The slit 34 should be wider than the width of the needle handle 26.

Figure 8:
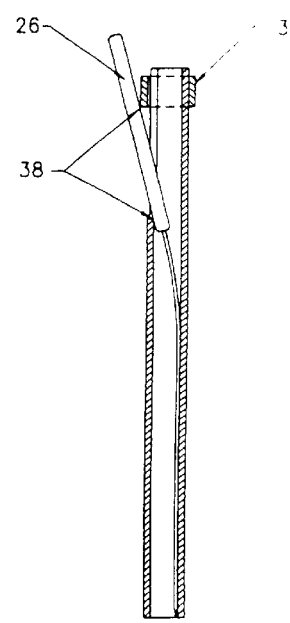
FIG. 8 is a fragmental sectional side view of the device in the direction of arrow B in FIG. 6.

FIG. 8 shows the needle handle 26 in a deflected position obtained by squeezing the needle handle between the lower edge 36 of the notch 30 and the lower edge 38 of the sleeve 32. Deflection of the handle 26 between the sleeve 32 and the notch 30 causes the needle to bend inside the guide tube 28, so that the needle 24 assumes a diagonal position, i.e. a position in which the handle 26 and the tip (not shown in FIG. 8) of the needle 24 are pushed to diametrically opposite sides inside the guide tube 28.

The device 15 of the invention operates as follows. The practitioner inserts an acupuncture needle 14 (FIG. 2) or 24 (FIG. 6) into the guide tube 12 or 28 so that the tip 11 of the needle 14 or 24 is positioned in flush with the lower edge of the guide tube. This can be achieved by resting the guide tube 12 or 28 vertically on a clean sterile surface and moving the needle 14 or 24 down until contact of the needle tip 11 with the surface is felt. The needle handle 16 or 26 is inserted into the slot or notch 18 (FIG. 3) or 30 (FIG. 6).

Figure 9:
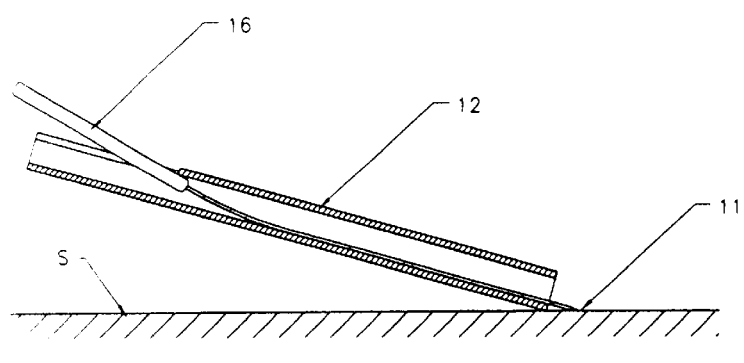
FIG. 9 is a view of the device of the invention with the needle for insertion in an inclined position.

Provision of the notch 18 or 30 allows the needle handle 16 or 26 to project outward from the upper end of the guide tube so that manipulation with the needle 14 or 24 is facilitated and the needle can be inserted to the required depth. In the case of inclined insertion shown in FIG. 9, the practitioner presses the needle handle 16 (26) to one side of the guide tube 12 so that the needle handle is bent to a position shown in FIG. 9, while the tip 11 of the needle on the other end of the guide tube 12 (24) is shifted to the opposite side of the guide tube. As a result, the needle assumes a "diagonal" position inside the guide tube. Provision of the chamfer 22 and the notch 18 (30) facilitates bending of the needle handle 16 (26) and allows the practitioner to insert the needle tip 11 to the required depth, irrespective of angle α.

In the case of the embodiment of FIGS. 5 and 6, the needle 24 can be fixed in a diagonal position inside the guide tube 28 by turning the sleeve 32 around the vertical axis of the tube 28 so that the slot 34 and the notch 30 will not be aligned. As a result, the needle handle 26 (FIG. 8) is fixed between the lower edge 38 of the sleeve 32 and the bottom of the notch 30. In this case, the opposite end of the needle, i.e., the needle tip 29 will be pushed to the inner wall of the guide tube 28 opposite to the position of the handle 26, i.e., to an inclined position. Now the needle can be pushed down for insertion into the patient's skin.

After insertion, the guide tube can be removed either by bringing the notch in the sleeve into the alignment with the notch in the tube and then sliding the tube off the needle, or by sliding the sleeve off the guide tube first and then removing the tube. Also, both notches—in the tube and in the sleeve—can be wide enough to allow the tube with the sleeve to be removed off the needle by pulling it up at the appropriate angle.

If the practitioner needs freedom for manipulation of the needle handle 26, he/she can turn the sleeve 32 to a position in which the slit 34 and the notch 30 are aligned. The sleeve 32 is shifted slightly upward, so that the needle handle 26 can be freely moved in a vertical slot formed by the slit 34 and the notch 30.

Thus it has been shown that the device of the invention provides an acupuncture device with an improved needle guide tube which allows convenient insertion of the needle irrespective of the angle of the needle to the surface of the patient's skin, ensures clearance between the end of the needle handle and the upper end of the guide tube sufficient for full and painless penetration of the needle into the patient's skin in the case of angular insertion, and has the means for maintaining the needle in a correct position with respect to the inner walls of the guide tube.

Although the invention has been described with reference to specific embodiments, it is understood that the invention is not limited by these embodiments and that any changes and modifications are possible, provided they do not depart from the scope of the attached patent claims. For example, the notch may have a shape other than triangular or rectangular, the needle handle may have a different configuration, the guide tube can be made of various materials such as transparent or non-transparent plastic or glass, and the sleeve can be made from a piece of plastic or rubber tube having a diameter different from the diameter of the guide tube.

What is claimed is:

1. An acupuncture device comprising:
   a needle having an outer diameter, a tip on one end, and a handle on the other end, said handle having a width;
   a guide tube having an inner diameter and a slot cut through the wall of said guide tube from one end of said guide tube in the longitudinal direction of said guide tube to a part of the length of said guide tube, said needle being inserted into said guide tube, said inner diameter of guide tube being greater than said outer diameter of said needle, and said slot at least on a part of its length has a width greater than said width of said handle; and means for shifting said handle toward one side of said guide tube and for shifting said tip towards the side of said guide tube opposite to said one side.

2. The device of claim 1, wherein said slot has a triangular shape.

3. The device of claim 1, wherein said slot has a rectangular shape.

4. The device of claim 1, wherein said means for shifting comprises a sleeve which is shorter than said guide tube and is slidingly fit onto said guide tube, said sleeve having a through slit in its side wall which extends in the axial direction of said sleeve, said slit in said sleeve being wider than said width of said handle.

5. The device of claim 4, where the edge of said guide tube is beveled in the area of said slot of said guide tube.

6. A method of acupuncture comprising:

providing an acupuncture device comprising an acupuncture needle with a tip on one end and a handle on the other end, a guide tube with a slot cut through the wall of said guide tube at one end of said tube, and means for shifting said handle toward one side of said guide tube and for shifting said tip towards the side of said guide tube opposite to said one side;

inserting said needle into said guide tube;

bending said handle into said slot of said guide tube, thus shifting said tip to the side of said guide tube opposite to said slot on said one end; and inserting said needle into a patient's skin by pressing on said handle.

7. A method of acupuncture with an inclined position of an acupuncture needle to the skin of a patient, comprising:

providing an acupuncture device comprising an acupuncture needle with a tip on one end and a handle on the other end, and a guide tube with a slot cut through the wall of said guide tube at one end of said tube;

Inserting said needle into said guide tube;

bending said handle into said slot of said guide tube, thus shifting said tip to the side of said guide tube opposite to said slot on said one end;

inclining said guide tube at an angle to the patient's skin to ensure an inclined position of said needle to the patient's skin; and inserting said needle into the patient's skin by pressing on said handle in said inclined position.

* * * * *